United States Patent [19]

Melanson, Jr. et al.

[11] Patent Number: 4,906,454

[45] Date of Patent: Mar. 6, 1990

[54] DEODORANT COMPOSITIONS CONTAINING SPECIFIC PIROCTONE SALTS AND PERFUMES

[75] Inventors: John D. Melanson, Jr., Alexandria, Ky.; Robert N. Sturm, Jr., Loveland, Ohio

[73] Assignee: The Procter & Gamble Company, Cincinnati, Ohio

[21] Appl. No.: 314,627

[22] Filed: Feb. 23, 1989

[51] Int. Cl.$^4$ .................. A61K 7/32; A61K 9/12; A61K 7/48

[52] U.S. Cl. ......................... 424/47; 424/65; 424/76.2; 424/76.4; 424/401; 514/336; 514/852; 514/859

[58] Field of Search .............. 514/336, 852, 859; 424/401, 47, 65, 76.2, 76.4

[56] References Cited

U.S. PATENT DOCUMENTS

| | | | |
|---|---|---|---|
| 3,972,888 | 8/1976 | Lohaus et al. | 260/297 Z |
| 4,185,106 | 1/1980 | Dittmar et al. | 514/336 |
| 4,278,658 | 7/1981 | Hooper et al. | 424/65 |
| 4,304,679 | 12/1981 | Hooper et al. | 252/106 |
| 4,322,308 | 3/1982 | Hooper et al. | 252/107 |
| 4,477,361 | 10/1984 | Sperti et al. | 252/106 |
| 4,621,090 | 11/1986 | Iwata | 514/332 |
| 4,631,187 | 12/1986 | Padden et al. | 514/852 |
| 4,686,211 | 8/1987 | Hara | 514/148 |
| 4,736,756 | 4/1988 | Grollier | 424/70 |
| 4,762,847 | 8/1988 | Edwards et al. | 514/859 |

FOREIGN PATENT DOCUMENTS

| | | |
|---|---|---|
| 58-180415 | 10/1983 | Japan . |
| 58-0222010 | 12/1983 | Japan . |
| 59-10506 | 1/1984 | Japan . |
| 60-23310 | 2/1985 | Japan . |
| 62-151499 | 7/1987 | Japan . |
| 63-139998 | 6/1988 | Japan . |
| 63-179813 | 7/1988 | Japan . |
| 2208149 | 3/1989 | United Kingdom . |

OTHER PUBLICATIONS

Lion C.A. 100: 73790A (1983) of Jpn, 58/180415, 21 Oct. 1983.
Lion C.A. 100: 144833E (1983) of Jpn, 58/222007, 23 Dec. 1983.
Lion C. A. 100: 144837J (1984) of Jpn, 59/10506, 20 Jan. 1984.
Lion C. A. 102: 209150T (1985) of Jpn, 60/23310, 5 Feb. 1985.
Molls C. A. 106: 89939r (1986).
Wakui C.A. 107: 223052x (1987) of Jpn 62/151499, 6 Jul. 1987.
Kamura C.A. 110: 141282v (1988) of Jpn 63/139998, 11 Jun. 1988.
Ueda C.A. 110: 160216t (1988) of Jpn 63/179813, 23 Jul. 1988.
Cosmetic and Drug Preservation (edited by J. Kabara 1984), 742–743.
Deodorant and Antiperspirant Formulatory, 100 Cosmetics and Toiletries, 65–68, Dec. 1985.
Perfuming Deodorants and Antiperspirants, 52 Soap Cosmetics Chemical Specialties 48, 50, 66, Sept. 1976.
The Merck Index 10th Edition, 1983.
Cosmetics: Science and Technology, vol. 2, 2nd Edition, Balsam and Sagarin, 1972.

*Primary Examiner*—Shep K. Rose
*Attorney, Agent, or Firm*—Steven J. Goldstein; Richard C. Witte

[57] ABSTRACT

Deodorant compositions comprising piroctone acid, its nonprimary olamine salts, metal salts and combination thereof; and a perfume which contains high concentrations of aldehydes and/or ketones are disclosed. These deodorants have good cosmetics, have minimized component interactions, and are excellent in the prevention of body malodors.

15 Claims, No Drawings

DEODORANT COMPOSITIONS CONTAINING SPECIFIC PIROCTONE SALTS AND PERFUMES

TECHNICAL FIELD

The present invention relates to effective body deodorant compositions having minimized negative interactions between the antimicrobial component and the aldehyde and ketone-containing perfumes utilized in the compositions.

BACKGROUND OF THE INVENTION

Human body malodors are believed to be partly created by bacterial attack on sweat gland secretions, which results in production of pungent fatty acids. To combat such malodors, soaps are used to cleanse the axilla (underarm area) of these odor-causing fatty acids and reduce the amount of bacteria found there. Although fatal to most, some bacteria survive the washing process and immediately start the production of malodors again.

Antimicrobial ingredients are frequently incorporated into treatments (e.g., soap bars or deodorants) which can be applied during or after washing to destroy bacteria which survive washing with soap alone. Among the antimicrobials used to combat bacterial growth are Octopirox, Triclosan, and Chlorhexidine; see Cosmetic and Drug Preservation (edited by J. Kabara 1984) 620-623. In general, however, even antimicrobial ingredients are not totally effective, in preventing formation of malodors. It is for this reason that perfumes historically have played an important role in deodorancy.

Perfumes generally provide some deodorancy by creating interference with the reception of malodors by the nose. U.S. Pat. No. 4,304,679, Hooper, issued Dec. 8, 1981; U.S. Pat. No. 4,322,308, Hooper, issued Mar. 30, 1981; and U.S. Pat. No. 4,477,361, Sperti, issued Oct. 16, 1984; teach that some perfumes, notably those having high levels of certain aldehyde and ketone components, can be used to neutralize or inhibit the development of body odors.

The combination of antimicrobials and perfumes, however, provides excellent deodorancy as it utilizes both mechanisms in one treatment to deter the development of malodors. This combination of antimicrobials and perfumes in deodorants is well known in the art; see "Antiperspirants and Deodorants", 2 Cosmetics, Science and Technology 400-410 (M. Balsam and E. Sagrin; editors, 1972); "Deodorant & Antiperspirant Formulary", 100 Cosmetics and Toiletries 65-68 (Dec. 1985); and Midwood, Perfuming Deodorants/Antiperspirants, 52 Soap Cosmetics Chemical Specialties 48, 50, 66 (Sept. 1976).

Japanese Laid Open Patents 58-0222010, published Dec. 23, 1983, and 60-023310, published Feb. 5, 1985, both to Lion, describe the use of hydroxy pyridone compounds, specifically the salts of piroctone acid, in deodorant compositions to combat production of malodors by the body. These compositions may include perfumes along with other conventional ingredients.

The most commonly used salts of piroctone acid (i.e., the primary olamine salts), such as Octopirox, interact negatively with perfumes which have significant concentrations of aldehydes and ketones. This is a particular problem since it is this interaction which blocks the ability of the aldehyde- and ketone-containing perfume components to inhibit the development of body odors.

It has now surprisingly been found that certain forms of piroctone acid do not interact negatively with perfume aldehydes and ketones. This invention thus describes specific piroctone salts which, when combined with a perfume containing high concentrations of aldehydes and ketones, form effective deodorant compositions. The deodorant compositions herein may be incorporated into products which may benefit from the use of an antimicrobial/perfume combination. Such products include laundry detergents, catamenials, bar soaps, bath gels, and personal deodorants.

Personal body deodorants may take the form of a solid, cream or liquid. These deodorant forms are delivered to the body via a variety of devices such as, canisters with elevating devices which hold a free standing solid product (sticks), aerosol sprays, pump sprays, and liquid applicators.

All percentages and ratios herein are by weight unless otherwise indicated.

SUMMARY OF THE INVENTION

The present invention provides a deodorant composition, comprising:

(a) from about 0.1% to about 1.0% of an antimicrobial ingredient selected from the group consisting of piroctone acid, metal salts of piroctone acid, secondary and tertiary olamine salts of piroctone acid, and mixtures thereof; and (b) from about 0.01% to about 7% of a perfume comprising from about 5% to about 50% of aldehydes and ketones (the preferred aldehyde being hexyl cinnamic aldehyde).

These deodorant compositions may be formulated into a variety of personal deodorant products, such as cosmetic sticks, sprays and body lotions/splashes. This invention also provides methods for treatment or prevention of malodors produced by the body.

DETAILED DESCRIPTION OF THE INVENTION

The components utilized in the present invention are described in detail below.

Antimicrobial Ingredient

To make an effective deodorant composition only certain forms of piroctone can be combined with ketone- and aldehyde-containing perfumes. The forms of piroctone used in the present invention include piroctone acid, metal salts of piroctone acid (such as the aluminum, sodium, potassium, zirconium, calcium and zinc metal salts), secondary and tertiary olamine salts of piroctone acid (such as the diethanolamine and triethanolamine salts), and mixtures thereof. The primary olamine salt of piroctone acid (known commercially as Octopirox) is not useful in the present invention since it interacts negatively with the aldehyde and ketone components contained in the perfume.

Piroctone compounds useful in this invention contain the basic 1-hydroxy-2-pyridone structure:

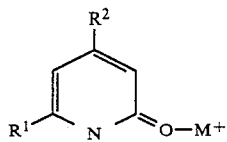

wherein $R^1$ is selected from $C_1$-$C_{17}$ hydrocarbon radicals, $R^2$ is selected from $C_1$-$C_4$ alkyl, $C_2$-$C_4$ alkenyl or alkynyl, hydrogen, phenyl or benzyl, and M is selected from hydrogen; metals including aluminum, calcium, potassium, sodium, zinc, and zirconium; diethanolamine (herein DEA) and triethanolamine (herein TEA). These piroctone materials are described in detail in Japanese Laid Open Patent 58-0222010, issued Dec. 23, 1983, and *Cosmetic and Drug Preservation* (edited by J. Kabara 1984) 742-743, both of which are incorporated herein by reference. Preferred $R^1$ group is $(CH_3)_3CCH_2CH(CH_3)CH_2$— and a preferred $R_2$ is methyl. Particularly preferred antimicrobials in this invention include piroctone acid, the sodium and potassium salts of piroctone acid, DEA and TEA salts of piroctone acid, and mixtures thereof. The piroctone antimicrobial comprises from about 0.1% to about 1.0%; preferably from about 0.2% to about 0.6%, of the deodorant composition.

Perfume

The perfume is an important component of the deodorant compositions defined by this invention. The compositions of the present invention contain from about 0.01% to about 7%, preferably about 1% to about 4%, of the specifically-defined perfume. Aldehydes and ketones must comprise from about 5% to about 50% of the perfume.

As disclosed in U.S. Pat. No. 4,322,308, Hooper et al., issued Mar. 30, 1982, and U.S. Pat. No. 4,304,679, Hooper et al., issued Dec. 8, 1981, both incorporated herein by reference, perfume components generally include, but are not limited to, phenolic substances (such as iso-amyl salicylate, benzyl salicylate, and thyme oil red); essence oils (such as geranium oil, patchouli oil, and petitgrain oil); extracts and resins (such as benzoin siam resinoid and opoponax resinoid); "synthetic" oils (such as Bergamot 37 and 430, Geranium 76, and Pomeransol 314); aldehydes and ketones (such as B-methyl naphthyl ketone, p-t-butyl-A-methyl hydrocinnamic aldehyde and p-t-amyl cyclohexanone); polycyclic compounds (such as Coumarin and B-naphthyl methyl ether); esters (such as diethyl phthalate, phenylethyl phenylacetate, and non-anolide-1:4); and alcohols (such as dimyrcetol, phenylethyl alcohol and tetrahydromuguol). In order to achieve the desired deodorant characteristics, the perfumes used in the present invention include relatively high levels of the aldehyde and ketone components. Examples of such components useful in perfumes herein include decyl aldehyde, undecyl aldehyde, undecylenic aldehyde, lauric aldehyde, amyl cinnamic aldehyde, ethyl methyl phenyl glycidate, methyl nonyl acetaldehyde, myristic aldehyde, nonalactone, nonyl aldehyde, octyl aldehyde, undecalactone, hexyl cinnamic aldehyde, benzaldehyde, vanillin, heliotropine, camphor, para-hydroxy phenolbutanone, 6-acetyl 1,1,3,4,4,6 hexamethyl tetrahydronaphthalene, alpha-methyl ionone, gamma-methyl ionone, and amyl-cyclohexanone and mixtures of these components.

The perfume conponents may be combined by those skilled in the perfumery arts to create a wide variety of fragrances. However, as described herein, all of the perfumes should contain relatively high levels of aldehydes and/or ketones, because it is these components which, when appropriately formulated, can inhibit development of body odors. An example of the type of perfume formulation useful in the deodorant compositions of the present invention follows.

| Component | Weight % |
|---|---|
| Ambrox | 2.51 |
| Benzambre II 30024 (Noville) | 5.50 |
| Benzyl Salicylate | 5.01 |
| Bouquet RS-14 | 3.51 |
| Coumarin | 2.16 |
| Geranium Bourbon | 3.51 |
| Hexyl Cinnamic Aldehyde | 10.00 |
| Iso Eugenol | 1.50 |
| La Moss 26657 | 7.00 |
| Linalyl Acetate | 5.01 |
| Menthol | 5.66 |
| Musk Xylol | 2.51 |
| Patchouli Oil | 4.01 |
| Sandalwood | 2.81 |
| 6-acetyl 1,1,3,4,4,6 hexamethyl tetrahydronaphthalene | 11.50 |
| Galaxolide 50% | Q.S. to 100.00 |

This composition contains about 10% of aldehyde and about 11% of ketone components. It will be appreciated that many other formulation variations are possible, as long as the required level of aldehyde/ketone is met.

It is particularly preferred that the aldehyde is hexyl cinnamic aldehyde. Preferred perfume compositions contain from about 5% to about 50% of hexyl cinnamic aldehyde. U.S. Pat. No. 4,477,361, Sperti et al., issued Oct. 16, 1984, and U.S. Pat. No. 4,304,679, Hooper et al., issued Dec. 8, 1981, describe a variety of perfumes which can include hexyl cinnamic aldehyde.

The deodorant compositions of the present invention may be manufactured in a variety of product forms, such as those described below.

Stick Deodorants

The deodorant compositions described in this invention may be formulated as deodorant sticks. Soap-based cosmetic sticks are described in U.S. Pat. No. 2,857,315, Teller, issued Oct. 21, 1958, and U.S. Pat. No. 2,900,306, Slater, issued Aug. 18, 1959, both of which are incorporated herein by reference. These sticks utilize soap as a gelling agent to form a firm gel matrix with good consumption characteristics.

The stick deodorants herein contain a gelling agent selected from, for example, sodium and potassium salts of fatty acids containing from about 12 to 18 carbon atoms (i.e., soaps). Most preferred is the sodium salt of stearic acid. These gelling agents generally comprise from about 3% to about 10%, preferably from about 4% to about 8%, of the stick composition.

Another essential component of the stick is a polyhydric alcohol which solubilizes the gelling agent, allowing the medium to gel. Examples of suitable polyhydric alcohols for use herein include ethylene glycol, propylene glycol, dipropylene glycol, trimethylene glycol, butylene glycol, hexylene glycol, glycerine, and mixtures thereof. Most preferred is dipropylene glycol. The polyhydric alcohol herein preferably comprises from about 5% to about 90%; preferably from about 10% to about 90%; and most preferably from about 10% to about 80% of the stick's composition.

Optional components for use in deodorant sticks include a variety of ingredients to improve composition, efficacy, stability, cosmetics, and aesthetics. Such optional components include, for example, monohydric alcohols, coupling agents, dyes, pigments, coloring agents, emollients, alcohol evaporation retardants, and water.

Monohydric alcohols, used at levels of from about 0% to about 70%, preferably from about 5% to about 70% of the composition, impart cosmetic advantages such as cool feel to the skin and a strong scent which confirms the deodorant's presence to the user. Suitable monohydric alcohols include methanol, ethanol, isopropanol, and mixtures thereof; preferred is ethanol.

Coupling agents, also known as emulsifiers, as used herein, means any compound or composition which acts to bring polar, intermediate polar and non-polar components of the stick composition into a homogenous mixture. The deodorant stick's coupling agents include, for example, polyethylene glycol (PEG), polypropylene glycol (PPG), and the PEG/PPG ethers of $C_4$–$C_{22}$ (preferably $C_{10}$–$C_{20}$) fatty alcohols; the most preferred is PPG-3 myristyl ether. The emulsifier comprises from about 5% to about 60%, preferably from about 10% to about 50%, and most preferably from about 15% to about 30%, of the stick composition.

Dyes, pigments and coloring agents may be used to achieve an aesthetically pleasing appearance and reinforce the product's concept goals. The dyes selected are those ceritified for use in drugs and cosmetic products. Said dyes, pigments and coloring agents generally comprise from about 1 ppm to about 10 ppm of the finished composition.

An emollient may be included to provide lasting dry feel to the skin and reduce tackiness. These emollients are, for example, selected from the group consisting of volatile and nonvolatile silicones; fatty alcohols; esters formed by the reaction of $C_3$–$C_{18}$ fatty alcohols with $C_3$–$C_{18}$ fatty acids, such as di-isopropyl adipate, isopropyl myristate, isopropyl palmitate, glycerol monostearate, and $C_{12}$–$C_{15}$ alcohol lactates; preferred are the volatile silicones, such as cyclomethicone. The emollient comprises from about 10% to about 30% of the composition.

To prevent shrinkage of the stick resulting from the loss of alcohols, alcohol evaporation retardants may be included in the formula. These are generally polyhydric alcohols, such as glycerine, sorbitol, and mixtures thereof.

Finally, water may be added to assist in incorporation of dry materials into the soap/gel phase matrix. Water typically does not exceed 30% of the total weight of the stick.

Liquid Deodorants

The deodorants of the present invention may also be formulated as a liquid. Such deodorants may be incorporated in a variety of different delivery systems, including aerosol sprays, pump sprays, lotions, and splashons.

Aerosol sprays have gained wide consumer acceptance. These sprays typically are anhydrous systems comprising deodorant compositions which are homogeneously dispersed in a liquid solvent vehicle together with a liquified volatile propellant in a pressurized aerosol container. The liquid solvent vehicle is selected from the group which consists of monohydric alcohols, non-volatile solvents, water, and mixtures thereof, and comprises from about 10% to about 80%, preferably from about 50% to about 80%, of the final composition.

The aerosol spray, created by rapid evaporation of the propellant upon dispensing from the atomizing valve, provides effective delivery of the deodorant composition to the targeted area. Useful aerosol containers are described in U.S. Pat. No. 3,083,917 and U.S. Pat. No. 3,083,918, Abplanalp et al., issued Apr. 2, 1963, and U.S. Pat. No. 3,544,258, Presant et al., issued Dec. 1, 1970, all of which are incorporated herein by reference.

Propellants used in the aerosol sprays typically have a boiling point within the range from about −45° C. to about 5° C. The aerosol propellants are liquified when packaged in conventional aerosol containers under pressure. Aerosol propellants include chemically inert hydrocarbons, such as propane, n-butane, isobutane, and cyclopropane, and mixtures thereof, as well as halogenated hydrocarbons, such as dichlorodifluoromethane (propellant 12), 1,1-dichloro-1,1,2,2-tetrafluoroethane (propellant 114), 1-chloro-1,1-difluoroethylene (propellant 142-B), 1,1-difluoroethane (propellant 152-A), monochlorodifluoromethane (propellant 22), 1-chloro-1,1-difluoro-2,2,2-trifluoroethane (propellant 115), and mixtures thereof, all of which are commercially available from E. I. DuPont deNemours and Co. Isobutane, used singly or admixed with other hydrocarbons, is preferred for use in the present aerosol deodorant composition. The propellant comprises from about 20% to about 50%, preferably from about 25% to about 40%, of the total weight of the composition.

Although popular, deodorant aerosol sprays may present several cosmetic problems. For example, they may create a cooling sensation when applied to the skin, as well as a feeling of wetness once applied. In addition to the cosmetic considerations, the possible impact of the use of aerosol propellants on the environment has created momentum for the development of non-aerosol sprays.

Non-aerosol sprays, also known as pump sprays, are well known in the art. See U.S. Pat. No. 4,053,581, Pader et al., issued Oct. 11, 1977; U.S. Pat. No. 4,065,564, Miles et al., issued Dec. 27, 1977; and U.S. Pat. No. 4,073,880, Pader et al., issued Feb. 14, 1978; all of which are incorporated herein by reference. These patents describe liquid antiperspirant compositions which are suitable for use in pump sprays. The spray technology which is modified to include the antimicrobials and perfumes described above falls within the scope of the present invention. Except for the propellant, the pump spray deodorants utilize the same basic formula as the aerosol sprays.

Other forms of the liquid deodorants include body lotions and splashes which may be delivered to the skin manually or through the use of an applicator system. Their formula is basically the same as that of the pump sprays, with the lotion having a slightly greater viscosity than the splash. Viscosity may be adjusted by incorporation of fillers such as silica, or use of high molecular weight polydimethylsiloxanes, such as dimethicone, as the non-volatile solvent vehicle.

All of the liquid deodorants previously described in the present application contain a liquid solvent vehicle selected from the group consisting of monohydric alcohols, non-volatile solvents, water, and mixtures thereof. The non-aerosol liquid deodorants contain liquid solvent vehicle from about 65% to about 99%. Also, a variety of ingredients to improve consistency, efficacy, stability, cosmetics, and aesthetics of the deodorant product may be utilized. Such ingredients include, for example, coupling agents, dyes, pigments, coloring agents, emollients, and mixtures thereof.

Monohydric alcohols are used herein as a liquid solvent vehicle which impart cosmetic advantages such as cool feel to the skin and strong scent confirming the deodorant's presence to the user. Examples of suitable monohydric alcohols include methanol, ethanol, isopropanol, and mixtures thereof; preferred is ethanol. The monohydric alcohol comprises from about 10% to about 80%, preferably from about 15% to about 45% of the non-aerosol liquid deodorant compositions; and from about 50% to about 80% in the aerosol spray.

The non-volatile solvent is a liquid solvent vehicle which slows the evaporation of the perfuming components in the deodorant composition after application. Suitable non-volatile solvents include non-volatile silicones, polyhydric alcohols, and mixtures thereof, and comprise from about 0% to about 50%, preferably from about 5% to about 30%, of the composition.

The non-volatiles silicones used herein are polyorganosiloxanes with viscosity ranging from about 10 centistokes to about 350 centistokes. The basic monomer unit

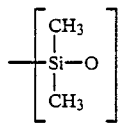

may repeat in a linear arrangement or in a cyclic structure. Such silicone oils include polyalkylsiloxanes, polyalkylarylsiloxanes, and polyethersiloxane copolymers. Such polyalkylsiloxanes include the Vicasil series (sold by General Electric Company) and the Dow Corning 200 series (sold by Dow Corning Corporation). Polyalkylarylsiloxanes include polymethylphenylsiloxanes having viscosities from about 15 to about 65 centistokes at 25° C. These are available, for example, as SF 1075 methylphenyl fluid (sold by General Electric Company) and 556 Cosmetic Grade Fluid (sold by Dow Corning Corporation). Preferred is dimethicone having a viscosity of about 100 centistokes.

Preferred polyhydric alcohols useful in the present invention are selected from the group consisting of ethylene glycol, propylene glycol, dipropylene glycol, trimethylene glycol, glycerine, and mixtures thereof. Most preferred is dipropylene glycol.

The last liquid solvent vehicle for use in the liquid deodorant is water. It is used to assist in incorporating dry materials into the deodorant liquid. Typically water will not exceed about 60% of the total compositions.

Coupling agents, also known as emulsifiers, include any compound or compositions which act to bring polar, intermediate polar, and non-polar components of the deodorant composition into a homogeneous mixture. Such agents include, for example, polypropylene glycol (PPG), polyethylene glycol (PEG), and the PPG/PEG ethers of $C_4$–$C_{22}$ (preferably $C_{10}$–$C_{20}$) fatty alcohols; most preferred is PPG-3 myristyl ether. Emulsifiers or coupling agents comprise from about 0% to about 50%, more preferably from about 5% to about 35%, and most preferably from about 8% to about 25%, of the liquid compositions.

Dyes, pigments, and coloring agents are used to achieve an aesthetically pleasing appearance and reinforce the product concept goals. The dyes selected are those certified for use in drug and cosmetic products. Said dyes, pigments, and coloring agents comprise from about 1 ppm to about 10 ppm of the composition.

An emollient may be included to reduce tackiness and provide lasting dry feel to the skin. The emollient comprises from about 0% to about 50%, preferably from about 5% to about 30%, of the composition. These emollients are selected from the group consisting of volatile and non-volatile silicones; fatty alcohols; esters formed by the reaction of $C_3$ to $C_{18}$ fatty alcohols with $C_3$ to $C_{18}$ fatty acids, such as diisopropyl adipate, isopropyl myristate, isopropyl palmitate, glyceryl monostearate, and $C_{12}$–$C_{15}$ alcohol lactates.

Preferred emollients in this invention are volatile silicones which may be a series of cyclic or linear monomer units. A description of various volatile silicones is found in Todd, et al., "Volatile Silicone Fulids for Cosmetics", 91 *Cosmetic and Toiletries*, 27–32 (1976), incorporated herein by reference. Preferred volatile silicone oils include those having from about 1 to about 9 silicon atoms, preferably containing from about 4 to about 5 silicon atoms. Cyclic volatile silicones useful herein include those of the following formula:

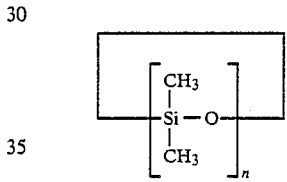

wherein n=3 to 9. Linear volatile silicone oils include those of the formula:

$$(CH_3)_3Si-O-[Si(CH_3)_2-O]_n-Si(CH_3)$$

wherein n=1 to 9. Linear volatile silicones generally have viscosities of less than about 5 centistokes at 25° C., whereas the cyclic silicones have viscosities of less than about 10 centistokes. Examples of volatile silicone oils useful in the present invention include: Dow Corning 344, Dow Corning 345 and Dow Corning 200 (sold by Dow Corning Corporation); 7207 and 7158 (sold by General Electric Company); and SWS-03314 (sold by SWS Silicones Corporation). Most preferred are the cyclic silicones with less than 6 monomer units, such as cyclomethicone.

The processes for incorporating the deodorant compositions into various delivery systems, as well as the equipment used in such processes, are well known to those skilled in the art. They may be batch processes (i.e., involving discrete processing steps) or continuous processing (i.e., wherein the product composition is passed between processing steps in essentially continuous increments).

Different processes are selected based upon the delivery system utilized. For example, making a liquid deodorant (other than the aerosol) requires no specific temperature conditions or order by which the components are combined. You may mix only the perfume and antimicrobial first and then add to the remainder of ingredients or just combine all the ingredients simultaneously. Similarly, the aerosol spray is prepared by combining all ingredients except propellant in an aerosol can and then adding the propellant under pressure. In contrast, sticks require specific processing temperatures to form the gel matrix. Normally, all stick ingredients, except for the perfume and color, are combined and heated from about 80° C. to about 95° C. The mixture is then cooled to about 70° C. before adding perfume and color in order to avoid evaporation of the fragrance and color degradation during processing.

The deodorant compositions described herein are utilized in conventional ways to treat or prevent the development of malodors in the axillary area of the human body. Specifically, an effective amount of the deodorant composition is applied topically to the axillary areas one or more times a day using any of the delivery systems previously described. When this is done, malodors are effectively prevented from developing without sacrificing good aesthetics upon application for the user.

EXAMPLES

The following nonlimiting examples illustrate the components and methods of the present invention.

EXAMPLE 1

A deodorant stick of the present invention is prepared as follows. All materials listed below, except for perfume and color, are combined in a vessel and heated to about 80° C. to 95° C. The solution is then cooled to about 70° C., and the perfume and color are mixed in. The solution is then poured into a stick mold and allowed to solidify.

| Component | Weight % |
|---|---|
| Piroctone Acid | 0.38% |
| Perfume (contains about 15% aldehydes and ketones, including hexyl cinnamic aldehyde) | 1.40% |
| Sodium Stearate | 7.00% |
| Dipropylene Glycol | 60.00% |
| Propylene Glycol | 27.00% |
| Water | 4.00% |
| Color Solution (0.1% in water) | 0.22% |

EXAMPLE 2

A deodorant stick of the present invention is prepared as described in Example 1.

| Component | Weight % |
|---|---|
| Sodium Piroctone | 0.41% |
| Perfume (contains about 10% hexyl cinnamic aldehyde as the aldehyde/ketone component) | 1.40% |
| Sodium Stearate | 7.00% |
| Propylene Glycol | 70.00% |
| Water | 20.97% |
| Color Solution (0.1% in water) | 0.22% |

EXAMPLE 3

A deodorant stick of the present invention is prepared as described in Example 1.

| Component | Weight % |
|---|---|
| Piroctone Diethanolamine | 0.50 |
| Perfume (contains about 10% hexyl cinnamic aldehyde as the aldehyde/ketone component) | 1.40 |
| Sodium Stearate | 6.00 |
| Dipropylene Glycol | 28.40 |
| PPG-3 Myristyl Ether | 21.00 |
| Cyclomethicone | 18.28 |
| Ethanol | 24.00 |
| Color Solution (0.01% in water) | 0.42 |

EXAMPLE 4

A deodorant stick of the present invention is prepared as described in Example 1.

| Component | Weight % |
|---|---|
| Piroctone Triethanolamine | 0.50 |
| Perfume (contains about 10% hexyl cinnamic aldehyde as the aldehyde/ketone component) | 1.40 |
| Sodium Stearate | 6.00 |
| Propylene Glycol | 12.00 |
| PPG-3 Myristyl Ether | 28.00 |
| PPG-10 Cetyl Ether | 10.00 |
| Cyclomethicone | 33.68 |
| Ethanol | 8.00 |
| Color Solution (0.01% in water) | 0.42 |

EXAMPLE 5

An aerosol deodorant spray of the present invention is prepared by combining all the ingredients except propellant in a standard aerosol can. The propellant is then added under pressure and the can is sealed.

| Component | Weight % |
|---|---|
| Piroctone Acid | 0.38% |
| Perfume (contains about 25% aldehydes and ketones) | 1.40% |
| Glycerine | 0.70% |
| Isopropyl Myristate | 0.70% |
| Dipropylene Glycol | 3.50% |
| Ethanol | 63.32% |
| 1,1-Difluoroethane (propellant) | 30.00% |

EXAMPLE 6

A pump spray deodorant of the present invention is prepared by first combining ethanol and piroctone diethanolamine to form a solution and then mixing in the remainder of the ingredients until uniform. The liquid is then packaged in a pump sprayer container.

| Component | Weight % |
|---|---|
| Piroctone Diethanolamine | 0.50% |
| Perfume (contains about 15% aldehydes and ketones, including about 10% hexyl cinnamic aldehyde) | 1.40% |
| Ethanol | 41.00% |
| Glycerin | 5.00% |
| Water | 52.10% |

The compositions described in Examples 1-6, when applied to the axillary area of a human in an effective amount, provide treatment and prevention of body malodors. The compositions themselves are stable without negative interaction between the perfume and antimicrobial active components.

What is claimed is:

1. A deodorant composition consisting essentially of:
   (a) from about 0.1% to about 1.0% of an antimicrobial ingredient effective to combat production of malodors by the body, other than the primary olamine salt piroctone acid, selected from the group consisting of piroctone acid, metal salts of piroctone acid, secondary and tertiary olamine salts of piroctone acid, and mixtures thereof; and
   (b) from about 0.01% to about 7% of a perfume effective to inhibit development of body odors comprising from about 5% to about 50% of components selected from the group consisting of aldehydes, ketones and mixtures thereof whose ability to inhibit development of body odors is blocked by a negative interaction with primary olamine salts of piroctone acid.

2. A deodorant composition according to claim 1 wherein the perfume comprises from about 5% to about 50% of aldehydes and ketones selected from the group consisting of decyl aldehyde, undecyl aldehyde, undecylenic aldehyde, lauric aldehyde, $C_{19}$–$C_{20}$ aldehyde, amyl cinnamic aldehyde, ethyl methyl phenyl glycidate, methyl nonyl acetaldehyde, myristic aldehyde, nonalactone, nonyl aldehyde, octyl aldehyde, undecalactone, hexyl cinnamic aldehyde, benzaldehyde, vanillin, heliotropine, camphor, para-hydroxy phenolbutanone, 6-acetyl 1,1,3,4,4,6 hexamethyl tetrahydronaphthalene, alpha-methyl ionone, gamma-methyl ionone, amylcyclohexanone, and mixtures thereof.

3. A deodorant composition according to claim 1 wherein the antimicrobial ingredient is selected from the group consisting of piroctone acid, the sodium and potassium salts of piroctone acid, the diethanolamine and triethanolamine salts of piroctone acid, and mixtures thereof.

4. A deodorant composition according to claim 1 wherein the aldehyde is hexyl cinnamic aldehyde.

5. A deodorant composition according to claim 3 where the aldehyde is hexyl cinnamic aldehyde.

6. A deodorant composition according to claim 1 in the form of a stick additionally comprising from about 3% to about 10% of a gelling agent, and from about 10% to about 90% of a polyhydric alcohol.

7. A deodorant composition according to claim 5 in the form of a stick additionally comprising from about 3% to about 10% of a gelling agent, and from about 10% to about 90% of a polyhydric alcohol.

8. A deodorant stick according to claim 6 wherein the polyhydric alcohol is selected from the group consisting of ethylene glycol, propylene glycol, dipropylene glycol, trimethylene glycol, butylene glycol, hexylene glycol, glycerine, and mixtures thereof, and the gelling agent is selected from the group consisting of sodium and potassium salts of $C_{12}$–$C_{18}$ fatty acids, and mixtures thereof.

9. A deodorant composition according to claim 1 in the form of an aerosol spray additionally comprising from about 10% to about 80% of a liquid solvent vehicle selected from the group consisting of monohydric alcohols, non-volatile solvents, water, and mixtures thereof; and from about 20% to about 50% of a propellant.

10. A deodorant composition according to claim 5 in the form of an aerosol spray additionally comprising from about 10% to about 80% of a liquid solvent vehicle selected from the group consisting of monohydric alcohols, non-volatile solvents, water, and mixtures thereof; and from about 20% to about 50% of a propellant.

11. A deodorant composition according to claim 9 wherein the liquid solvent vehicle is a monohydric alcohol selected from the group consisting of methanol, ethanol, isopropanol and mixtures thereof, and the propellant is selected from propane, n-butane, isobutane, cyclopropane, dichlorodifluoromethane, 1,1-dichloro-1,1,2,2-tetrafluoroethane, 1-chloro-1,1-difluoroethylene 1,1-difluoroethane, monochlorodifluoromethane, 1-chloro-1,1-difluoro-2,2,2-trifluoroethane, and mixtures thereof.

12. A deodorant composition according to claim 1 in the form of a liquid additionally comprising from about 65% to about 99% of a liquid solvent vehicle selected from the group consisting of monohydric alcohols, non-volatile solvents, water, and mixtures thereof.

13. A deodorant composition according to claim 5 in the form of a liquid additionally comprising from about 65% to about 99% of a liquid solvent vehicle selected from the group consisting of monohydric alcohols, non-volatile solvents, water, and mixtures thereof.

14. A deodorant composition according to claim 13 wherein the liquid solvent vehicle is selected from the group consisting of methanol, ethanol, isopropanol, ethylene glycol, propylene glycol, dipropylene glycol, trimethylene glycol, glycerine, polydimethylsiloxanes having a viscosity of from about 10 centistokes to about 350 centistokes, water, and mixtures thereof.

15. A method for treating or preventing malodors associated with human underarm perspiration, said method comprising applying to the axillary skin of a human a safe and effective amount of a deodorant composition according to claim 1.

* * * * *